United States Patent
Clark et al.

(10) Patent No.: US 11,720,704 B1
(45) Date of Patent: Aug. 8, 2023

(54) SYSTEM AND METHOD FOR AUTHENTICATING ACCESS TO PRIVATE HEALTH INFORMATION

(71) Applicant: Cigna Intellectual Property, Inc., Wilmington, DE (US)

(72) Inventors: Jonathan Clark, Tolland, CT (US); Steven J. Mastrianni, Colchester, CT (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 196 days.

(21) Appl. No.: 17/009,409

(22) Filed: Sep. 1, 2020

(51) Int. Cl.
| | |
|---|---|
| H04L 9/08 | (2006.01) |
| G06F 21/62 | (2013.01) |
| H04L 9/40 | (2022.01) |
| G10L 17/22 | (2013.01) |
| G16H 10/60 | (2018.01) |

(52) U.S. Cl.
CPC .......... *G06F 21/6245* (2013.01); *G10L 17/22* (2013.01); *G16H 10/60* (2018.01); *H04L 63/083* (2013.01); *H04L 63/0853* (2013.01); *H04L 63/0861* (2013.01); *H04L 63/102* (2013.01)

(58) Field of Classification Search
CPC ..... G06F 21/6245; G10L 17/22; G16H 10/60; H04L 63/083; H04L 63/0853; H04L 63/0861; H04L 63/102
USPC .......................................................... 726/7
See application file for complete search history.

(56) References Cited

U.S. PATENT DOCUMENTS

| | | | |
|---|---|---|---|
| 7,661,146 | B2 | 2/2010 | Karimzadeh |
| 10,049,661 | B2 | 8/2018 | Flaks |
| 10,331,852 | B2 | 6/2019 | Dormer |
| 10,410,630 | B2 | 9/2019 | Weng |
| 10,650,055 | B2 | 5/2020 | Vierra |
| 2001/0039503 | A1 | 11/2001 | Chan |
| 2006/0184455 | A1 | 8/2006 | Meyer |
| 2007/0101409 | A1 | 5/2007 | Palekar |
| 2007/0185718 | A1 | 8/2007 | Di Mambro |
| 2009/0037470 | A1 | 2/2009 | Schmidt |
| 2011/0178931 | A1 | 7/2011 | Kia |
| 2012/0123786 | A1 | 5/2012 | Valin |
| 2013/0086390 | A1 | 4/2013 | Kennedy |
| 2013/0167249 | A1 | 6/2013 | Birtwhistle |

(Continued)

FOREIGN PATENT DOCUMENTS

WO    2016090091 A1    6/2016

*Primary Examiner* — Jeffrey C Pwu
*Assistant Examiner* — Nega Woldemariam
(74) *Attorney, Agent, or Firm* — The Small Patent Law Group (57) ABSTRACT

A method for authenticating access to private health information (PHI) includes receiving a converted version of a spoken initiation of a retrieval of PHI. The method also includes requesting out-of-band authentication information from a user. The out-of-band authentication information that is requested contains different information than the spoken initiation of the retrieval of the PHI. The method also includes determining whether the out-of-band authentication information received from the user satisfies an authentication criterium associated with the user, obtaining the PHI requested by the user via the spoken initiation provided to the first device responsive to the out-of-band authentication information, and presenting the PHI requested by the user via the first device.

22 Claims, 3 Drawing Sheets

(56) References Cited

U.S. PATENT DOCUMENTS

| | | |
|---|---|---|
| 2013/0227712 A1 | 8/2013 | Salem |
| 2016/0328576 A1* | 11/2016 | Howley ................ G06F 3/0482 |
| 2017/0068785 A1 | 3/2017 | Experton |
| 2018/0256041 A1 | 9/2018 | Dormer |
| 2018/0276248 A1 | 9/2018 | Burkett |
| 2018/0352440 A1 | 12/2018 | Ballard |
| 2019/0068675 A1 | 2/2019 | Dowlatkhah |
| 2019/0103115 A1 | 4/2019 | Lesso |
| 2019/0130082 A1* | 5/2019 | Alameh .............. G06F 21/6218 |
| 2019/0272898 A1 | 9/2019 | Dormer |
| 2020/0082930 A1 | 3/2020 | De Francesco |
| 2020/0168306 A1 | 5/2020 | Chen |
| 2020/0294042 A1* | 9/2020 | Day ..................... G07F 19/201 |
| 2021/0209249 A1 | 7/2021 | Hoffer |

* cited by examiner

SYSTEM AND METHOD FOR AUTHENTICATING ACCESS TO PRIVATE HEALTH INFORMATION

FIELD

This application relates to controlling access to private health information.

BACKGROUND

Many devices can now interact with users using voice commands. For example, ALEXA-enabled products provided by AMAZON.COM, SIRI-enabled products provided by Apple Inc., and the like, can verbally interact with users to provide the users with news reports, weather reports, interactive games, and the like.

Some information, however, currently may not be able to be provided through such voice command-controlled devices. For example, confidential and/or private information, such as private health information (PHI), currently may not be able to be provided to users via voice command-controlled devices as the confidentiality and privacy of the devices audibly presenting the PHI may not be able to be controlled. These devices currently are unable to authenticate access to PHI or other confidential information.

As a result, some types of confidential information may not be accessible by these types of devices, either for presentation to users and/or for use in other applications.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Example methods and systems for authenticating access to PHI are provided. These methods and systems can allow for some electronic devices, such as voice command-controlled devices, to verbally interact with users and provide confidential and/or private information, such as private health information, to users via the devices. But, not all embodiments of the inventive subject matter are limited to authenticating access to PHI. One or more embodiments may be used to provide access to other confidential and/or private information, such as financial information (e.g., account information, purchase histories, tax returns, etc.), insurance information (e.g., insurance claims, insurance benefits, etc., whether healthcare insurance, home insurance, auto insurance, life insurance, or the like), educational information (e.g., report cards, grades, etc.), criminal information (e.g., criminal records, etc.), or the like. Additionally, while some examples focus on pharmaceutical data as being the PHI, the PHI can include other healthcare information, such as patient medical records. While examples and embodiments are described herein with PHI as the private and/or confidential information, other types of confidential and/or private information may be substituted in the description of PHI.

Figure 1:
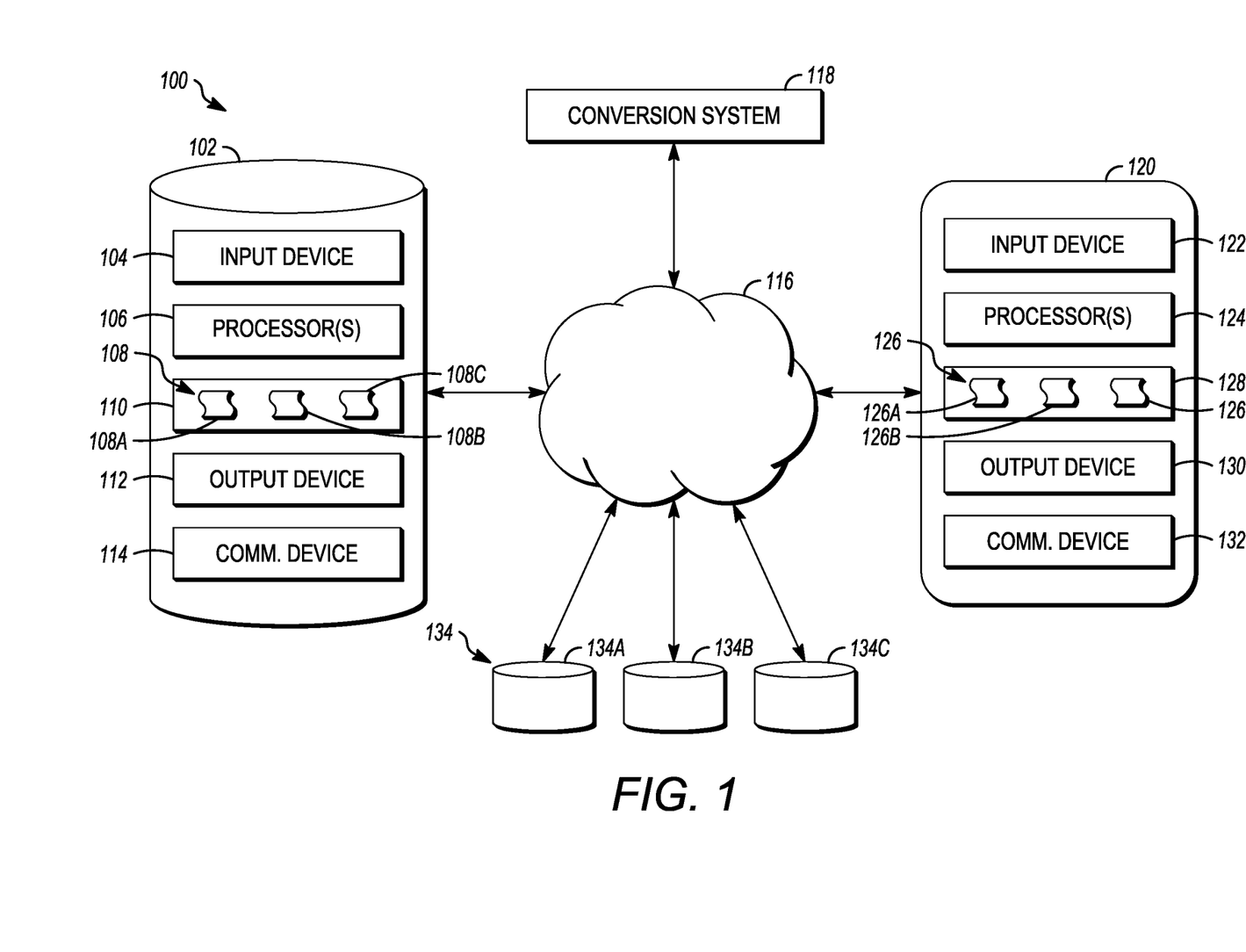
FIG. 1 illustrates one example of an authentication system.

FIG. 1 illustrates one example of an authentication system 100. The authentication system 100 may be used to provide access to electronic devices (e.g., voice command-controlled devices) to PHI so that these devices can audibly present the PHI to users. Optionally, the devices also can receive commands from users in response to audibly presenting the PHI. For example, the devices can receive verbal commands from the users to order a prescription refill, cancel an order of a prescription refill, schedule an appointment with a healthcare provider, open up an inquiry into a transaction involving a prescription, or the like. The devices can then implement the command, such as by ordering or canceling the refill, scheduling the appointment, sending the inquiry to the appropriate person(s) at a pharmacy benefit manager, or the like. This can significantly ease the burden on users to keep abreast of the PHI of the users and make transactions for the improved health and safety of the users. For example, authenticating access of the devices to PHI can make it easier for users to maintain or improve adherence to prescribed medications by simplifying the process for checking on prescription refills and ordering refills relative to current methods and techniques for checking and/or ordering refills.

The system 100 may include all or part of the components shown in FIG. 1 and described herein. A voice-controlled electronic device 102 can represent a computing device that is controlled to perform various operations based on instructions verbally provided by one or more users. The voice-controlled device 102 can include an input device 104 that receives vocal or audible input. The input device 104 can represent one or more microphones, piezoelectric bodies, or other audible pick-up devices. The voice-controlled device 102 can include one or more processors 106 that perform operations described in connection with the processors 106 and/or device 102, such as by implementing one or more sets of instructions 108 (such as software applications 108A-C) stored on a tangible and non-transitory computer readable medium 110, such as a computer memory. The processors 106 can represent one or more microprocessors, field programmable gate arrays, integrated circuits, microcontrollers, or the like.

The voice-controlled device 102 also can include an output device 112 that provides output to the user and/or other users. The output device 112 can represent a speaker that audibly presents the output, an electronic display that visually presents the output, or the like. A communication device 114 of the voice-controlled device 102 represents transceiving circuitry (e.g., one or more modems, antennas, transceivers, etc.) that communicate data via electronic signals with one or more other devices and/or systems. For example, the communication device 114 can allow the voice-controlled device 102 to communicate with other devices via one or more computer networks 116, such as the Internet, one or more intranets, etc. Examples of the network(s) 116 include Mobile Communications (GSM) networks, code division multiple access (CDMA) networks, 3rd Generation Partnership Project (3GPP), Internet Protocol (IP) networks, Wireless Application Protocol (WAP) networks, WiFi networks, or an IEEE 802.11 standards networks, as well as various combinations thereof. The networks 116 may include an optical network. The networks 116 may be a local area network or a global communication network, such as the Internet. In some embodiments, the networks 116 may include a network dedicated to prescription orders.

In one embodiment, one or more of the applications 108 can be performed by the processors 106 to receive audible commands (e.g., voice commands) from a user via the input device 104 as the spoken initiation, process the information contained in the audible commands to determine which PHI is requested, process the information to authenticate the user, and present the PHI to the user, as described herein.

The voice-controlled device 102 can receive a spoken initiation of a retrieval of via the input device 104. This spoken initiation can be a verbal trigger or request by a user (directed to the voice-controlled device 102) for some or all PHI associated with that user or another user. For example, a user can state "When can I get another prescription refill?", "Does this prescribed medicine have any contraindications with my other prescribed medications?", "When is my next doctor's appointment?", "What is the result of my blood test?", "What was my father's diagnosis?", and the like. This spoken initiation can be converted into a converted version of the information contained in the spoken initiation. For example, a first application 108A implemented by the processors 106 can record and send the spoken initiation (e.g., as one or more audio files) to a conversion system 118 via the one or more computer networks 116.

This conversion system 118 represents one or more computers that can translate or otherwise convert the audio recording of the spoken initiation into text. For example, the conversion system 118 can include computers that convert speech to text. Alternatively, the conversion system 118 can represent computers used by one or more operators to convert the speech to text. The text can be sent to a user-controlled electronic device 120 from the conversion system 118 (e.g., via the one or more computer networks 116).

The user-controlled electronic device 120 can represent another computer or computerized device that is separate from the voice-controlled device 102. The user-controlled electronic device 120 can represent a mobile phone, a tablet computer, a smartwatch, a laptop computer, a desktop computer, etc. The user-controlled electronic device 120 can include an input device 122 that receives input from a user. The input device 122 can represent one or more microphones, touchscreens, keyboards, styluses, buttons, cameras, fingerprint scanners, or the like. One or more processors 124 of the user-controlled electronic device 120 perform operations described in connection with the processors 124 and/or device 120, such as by implementing one or more sets of instructions 126 (such as software applications 126A-C) stored on a tangible and non-transitory computer readable medium 128, such as a computer memory. The processors 124 can represent one or more microprocessors, field programmable gate arrays, integrated circuits, microcontrollers, or the like.

The user-controlled electronic device 122 also can include an output device 130 that provides output to the user and/or other users. The output device 130 can represent a speaker, electronic display, or the like. In one example, the input device 122 and the output device 130 can both be embodied in a touchscreen. A communication device 132 of the user-controlled electronic device 120 represents transceiving circuitry (e.g., one or more modems, antennas, transceivers, etc.) that communicate data via electronic signals with one or more other devices and/or systems. For example, the communication device 132 can allow the user-controlled electronic device 120 to communicate with other devices via one or more computer networks 116.

The user-controlled electronic device 122 can receive the text converted from the spoken initiation. This text may be communicated in one or more data files from the conversion system 118 to the user-controlled device 122 and/or from the conversion system 118 to the voice-controlled electronic device 102 and then to the user-controlled device 122. One or more of the applications 126A-C can direct the processors 124 to examine the text and request out-of-band authentication information from a user.

The authentication information can be out-of-band information in that the information is not included in the spoken initiation provided to the device 102. Instead, the authentication information can be separately requested, and may include information that is not included in the spoken initiation. For example, the user-controlled electronic device 120 can request identifying information that is not included in the spoken initiation to verify that the user providing the authentication information has access and/or permission to access the PHI. This request for identifying information can include request for a unique code (a personal identification number, a numerical string, a text string, and/or an alphanumeric string provided by an authenticator application, such as one of the applications 126A-C, or from another source, such as printed on a pharmaceutical container like a pill bottle), a question for demographic information (e.g., a name of a relative or pet, a town or city, etc.), a question for a previously answered preference (e.g., the name of a friend, a favorite food or movie, a location where a spouse was met, etc.), or another question that seeks information that only the person authorized to receive the PHI is likely to have.

Optionally, the requested authentication information may include biometric data. For example, the requested authentication information can be a scan of a fingerprint of the user. The processors 124 of the user-controlled device 120 can display or play instructions that direct the user to place his or her finger or thumb into a touch-sensitive surface (e.g., a touchscreen, a fingerprint reader button, etc.) of the input device 122 or orient his or her thumb toward a camera of the input device 122. The input device 122 can scan the fingerprint of the finger or thumbprint of the thumb or examine an image of the fingerprint of the finger or thumbprint of the thumb. The fingerprint or thumbprint can be compared with previously authenticated fingerprints or thumbprints associated with the user or with the persons having access to the requested PHI. If the provided fingerprint or thumbprint matches the previously authenticated fingerprint(s) or thumbprint(s), then the authentication criteria may be determined to be satisfied.

As another example, the requested authentication information can be a retinal scan of the user. The processors 124 of the user-controlled device 120 can control a camera (or direct a user to use the camera) of the input device 122 to obtain a photo or other optically sensed information about the eye of the user. This information may be a retinal scan of the user, and the processors 124 can compare the retinal scan of the user with previously authenticated retinal scans associated with the user or with the persons having access to the requested PHI. If the provided retinal scan matches the previously authenticated retinal scan, then the authentication criteria may be determined to be satisfied.

As another example, vocal recognition can be used to authenticate the user's access to the PHI. The requested authentication information can be a voice sample of the user. The processors 124 of the user-controlled device 120 can control a microphone (or direct a user to use a microphone) of the input device 122 to obtain a recording of the user speaking a phrase supplied by the device 120 or another phrase. The processors 124 can record this vocal sample and compare the vocal sample of the user with previously authenticated vocal samples associated with the user or with the persons having access to the requested PHI. If the provided vocal sample matches the previously authenticated vocal sample, then the authentication criteria may be determined to be satisfied.

Optionally, the requested authentication information can include a combination of two or more of the above examples.

In an example embodiment, the out-of-band authentication can be received from the device, e.g., the user controlled device 120, separate from the voice activated device.

The user-controlled electronic device 120 can receive a user response to the request for authentication information and determine whether the provided authentication information satisfies an authentication criterium associated with the user having permission to access the PHI. For example, an application 126 operating on the user-controlled electronic device 120 can store or otherwise have access to approved codes and/or approved authentication information. These approved codes and/or approved authentication information can be compared with the information provided by the user to determine whether the user-provided information matches the approved codes and/or approved authentication information. If the information matches, then the user may be authenticated by the application 126 to access or otherwise receive the PHI via the voice-controlled device 102. If the information does not match, then the user may not be authenticated by the application 126 to access or otherwise receive the PHI via the voice-controlled device 102.

Different authentication criteria may be used for different types of PHI that are requested. For example, different authentication information may be requested depending on whether the spoken initiation seeks PHI of the user speaking the spoken initiation, or of another person (e.g., a parent, spouse, child, etc., of the user). The processors 124 can identify a patient of whose PHI is sought by the spoken initiation, such as by converting the spoken initiation to text or examining the text conversion of the spoken initiation. Depending on the name of the patient or the relationship of the patient to the user, the processors 124 can determine what authentication criteria is to be used. For example, a spoken initiation of "Tell me what my test result is" may result in the processors 124 requesting that the user provide a first set of information (e.g., an authentication code provided by an application 126) to confirm that the user has access to the PHI. But, if the spoken initiation seeks PHI of another person of "Tell me what my son's test result is," then the processors 124 may request additional or more information (e.g., a full name of the patient, a social security number of the patient, and/or a mailing address of the patient). This can help prevent or reduce the likelihood of dissemination of PHI of another person to the user when the user does not have permission to access the PHI.

As another example, different persons can have different authentication criteria. In a household, the parents may set the authentication criteria to request no information or very little information for requests for PHI involving the children, while the parents may set the authentication criteria to request additional or more complex information for requests for PHI involving the parents. As another example, a frequent user of the system 100 may set the authentication criteria to request no information or very little information for requests for PHI involving that user, while accessing the PHI of other users may require additional or more complex information. This can allow the frequent user to more easily access his or her frequently accessed PHI.

Alternatively, the system 100 may not rely on the user-controlled device 120 to obtain the authentication information. Instead, a different application 108 of the voice-controlled device 102 may be used to obtain the authentication information and determine whether the authentication information satisfies the authentication criteria. For example, a first application 108A can direct the processors 106 to record the spoken initiation and to obtain the text conversion of the spoken initiation, while a different, second application 108B can request the authentication information from the user and determine whether this authentication information satisfies the authentication criteria, as described above. Using separate applications 108 in this manner can help ensure that the person requesting the PHI has permission or access to the PHI before providing the PHI to the person.

The user-controlled device 120 can send an authentication signal to the voice-controlled device 102 (e.g., via the one or more networks 116) in response to determining that the user-provided information matches or satisfies the authentication criterium. One or more of the applications 108 can direct the processors 106 in the voice-controlled device 102 to obtain the PHI requested by the user via the spoken initiation. For example, the processors 106 can examine the text conversion of the spoken initiation (which may be communicated to the voice-controlled device 102 by the conversion system 118 and/or the user-controlled device 120) to determine what PHI is requested. Once the user is authenticated, the processors 106 communicate with one or more data stores 134 (e.g., data stores 134A-C) to obtain the requested PHI. The data stores 134 can represent different tangible and non-transitory computer readable media, such as computer servers, that store PHI.

For example, one or more of the data stores 134 can store pharmaceutical data used by a pharmacy benefit manager device to process claims for pharmaceutical benefits. This pharmaceutical data can include order data, member data, claims data, drug data, prescription data, and/or plan sponsor data. The order data may be related to a prescription order, and can include a type of the prescription drug (e.g., drug name and strength, etc.) and quantity of the prescription drug, etc. The order data may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like.

The order data can include verification information associated with fulfillment of the prescription in the pharmacy. For example, the order data may include videos and/or images taken of (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to transport prescriptions within the pharmacy may also be stored as order data.

The member data includes information regarding the members associated with the pharmacy benefit manager. The information stored as member data may include personal information, personal health information, protected health information, and the like. Examples of the member data include name, address, telephone number, e-mail address, prescription drug history, etc., and the like. The member data may include a plan sponsor identifier that identifies the plan sponsor associated with the member and/or a member identifier that identifies the member to the plan sponsor. The member data may include a member identifier that identifies the plan sponsor associated with the patient and/or a patient identifier that identifies the patient to the plan sponsor. The member data may also include, by way of example, dispensation preferences such as type of label, type of cap, message preferences, language preferences, or the like.

In some embodiments, the member data may include information for persons who are patients of the pharmacy but are not members in the pharmacy benefit plan being provided by the pharmacy benefit manager device. For example, these patients may obtain drug directly from the pharmacy, through a private label service offered by the pharmacy, a fulfillment center, or otherwise. In general, the use of the terms member and patient may be used interchangeably herein.

The claims data includes information regarding pharmacy claims adjudicated by the pharmacy benefit manager under a drug benefit program provided by the pharmacy benefit manager for one, or more than one, plan sponsors. In general, the claims data includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier number, medication class, the cost of the prescription drug provided under the drug benefit program, the copay/coinsurance amount, rebate information, and/or member eligibility, etc. Additional information may be included.

In some embodiments, other types of claims beyond prescription drug claims may be stored in the claims data. For example, medical claims, dental claims, wellness claims, or other type of health care-related claims for members may be stored as a portion of the claims data.

In some embodiments, the claims data includes claims that identify the members with whom the claims are associated. In some embodiments, the claims data includes claims that have been de-identified (e.g., associated with a unique identifier but not with a particular, identifiable member, etc.).

The drug data may include a drug name (e.g., technical name and/or common name, etc.), other names by which the drug is known by, active ingredients, an image of the drug (e.g., in pill form, etc.), and the like. The drug data may include information associated with a single medication or multiple medications.

The prescription data may include information regarding prescriptions that may be issued by prescribers on behalf of patients, who may be members of the pharmacy benefit plan, for example to be filled by a pharmacy. Examples of the prescription data include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

The plan sponsor data includes information regarding the plan sponsors of the pharmacy benefit manager. Examples of the plan sponsor data include company name, company address, contact name, contact telephone number, contact e-mail address, etc., and the like.

Other PHI data that can be stored in the data stores can include medical records, such as lab results, doctor notes in the records, demographic information, diagnoses, and the like.

Once the requested PHI is provided to the voice-controlled device 102, the processors 106 can direct the output device 112 to audibly present the requested PHI. The requested PHI can be converted to speech by the processors 106 via an audio file, and played on the output device 112 (e.g., a speaker). Because the user requesting the PHI was authenticated using out-of-band information, the user has established his or her permission to access the PHI and the PHI can be audibly presented to the user. This can allow for a much easier and straightforward way of obtaining a variety of PHI that may otherwise be cumbersome or time-consuming to obtain.

The audible presentation of the PHI may need to be limited in time, however. For example, the time period over which the authentication of the user to hear the PHI from the voice-controlled device 102 is granted may need to be limited (and not open-ended) to prevent others from being able to hear or obtain access to the PHI. In one embodiment, the voice-controlled device 102 may only allow the PHI to be audibly played for the user for a relatively short time period that the user may normally be within the same room as the device 102 (e.g., five minutes, fifteen minutes, etc.). This time period may have a default length or may be customizable by the user. For example, using the user-controlled device 120, the user may lengthen or shorten the time period over which the PHI can be played before another authentication is required. This modified time period can then be communicated to the voice-controlled device 102 from the user-controlled device 120.

The user may not want all of his or her PHI to be audibly presented by the voice-controlled device. For example, the user may only want some portion of the PHI to be audibly presented or may not want some other portion of the PHI to be audibly presented. The user can input limitations or instructions on which PHI is permitted to be played on the voice-controlled device 120. These limitations or instructions can define categories of PHI (e.g., prescription refill history, blood test results, DNA test results, healthcare provider appointments, etc.) that are allowed to be played on the voice-controlled device 102.

If the user-controlled device 120 or the voice-controlled device 102 determines that the PHI requested to be played by the user is outside of the defined allowable categories of PHI, then the user-controlled device 102 and/or the voice-controlled device 102 may not permit the requested PHI to be obtained and/or audibly presented via the voice-controlled device 102 but may allow PHI within the defined category or categories to be obtained and played.

Optionally, the user can input limitations or instructions on which PHI is not permitted to be played on the voice-controlled device 120. These limitations or instructions can define categories of PHI that are not allowed to be played on the voice-controlled device 102. If the user-controlled device 120 or the voice-controlled device 102 determines that the PHI requested to be played by the user is outside of the defined allowable categories of PHI, then the user-controlled device 102 and/or the voice-controlled device 102 may permit the requested PHI to be obtained and audibly presented via the voice-controlled device 102, but can prevent PHI within the defined category or categories from being obtained and/or played.

As another example, the user may restrict what PHI can be obtained and/or presented based on a time range. For example, the user may not want his or her entire lifetime of PHI to be presented via the voice-controlled device 102. The user may input a date range (via the device 102 and/or the device 120) that indicates that PHI obtained and/or entered into a record associated with the user at the data stores 134 within that range is allowed to be obtained and/or presented by the device 102. PHI obtained and/or entered into a record on a date outside of that user-defined date range is not permitted to be obtained and/or presented. PHI obtained and/or entered into a record on a date within the user-defined date range is permitted to be obtained and/or presented.

Optionally, the user may input a date range (via the device 102 and/or the device 120) that indicates that PHI obtained and/or entered into a record associated with the user at the data stores 134 within that range is not allowed to be obtained and/or presented by the device 102. PHI obtained and/or entered into a record on a date outside of that user-defined date range is permitted to be obtained and/or presented. PHI obtained and/or entered into a record on a date within the user-defined date range is not permitted to be obtained and/or presented.

As another example, a healthcare provider or one or more entities controlling the data stores 134 may restrict how long a user is authenticated to hear PHI. For example, the healthcare provider and/or entity controlling a data store 134 may only allow an authentication of a user by the device 102 and/or 120 to be valid for playing PHI for a designated period of time. Once that period of time expires following authentication of the user, the user may need to be authenticated again before the PHI is played on the device 120. In a situation where the user, the healthcare provider, and/or the entity controlling a data store 134 all provide different time periods over which an authentication is valid, the device 102 and/or 120 may use the shortest of these time periods. This can prevent a user, healthcare provider, or entity controlling a data store 134 to grant an authenticated user access to PHI for longer than another of the user, healthcare provider, or entity wants access to be granted.

As another example, the user may restrict what PHI can be obtained and/or presented based on a healthcare provider. For example, the user may not want his or her PHI associated or entered into a record by doctors other than a user-identified doctor to be presented via the voice-controlled device 102. The user may input an identification of one or more allowable healthcare providers (via the device 102 and/or the device 120) that indicates which PHI can be obtained and/or played via the device 120. If the PHI requested to be played on the device 120 by the user is provided or entered into a record by a healthcare provider that is one of the allowable healthcare providers, then the device 102 and/or the device 120 can allow the requested PHI to be obtained and/or played. If the PHI requested to be played on the device 120 by the user is not provided or entered into a record by a healthcare provider that is one of the allowable healthcare providers, then the device 102 and/or the device 120 can prevent the requested PHI to be obtained and/or played.

The user may input an identification of one or more disallowed healthcare providers (via the device 102 and/or the device 120) that indicates which PHI cannot be obtained and/or played via the device 120. For example, the user may not want the test result or associated PHI from a recent visit to a particular doctor to be audibly played for others to hear. If the PHI requested to be played on the device 120 by the user is provided or entered into a record by a healthcare provider that is one of the disallowed healthcare providers, then the device 102 and/or the device 120 can prevent the requested PHI from being obtained and/or played. If the PHI requested to be played on the device 120 by the user is not provided or entered into a record by a healthcare provider that is one of the disallowed healthcare providers, then the device 102 and/or the device 120 can allow the requested PHI to be obtained and/or played.

As another example, the user may restrict what PHI can be obtained and/or presented based on a healthcare benefit claim. For example, the user may only want the PHI associated with one or more types of claims for a healthcare benefit (e.g., within a healthcare insurance plan, a pharmacy benefit plan, a dental benefit plan, etc.) to be played, while PHI with other claims are not allowed to be obtained and/or played. The user may input an identification of one or more categories of benefit claims (via the device 102 and/or the device 120) that indicates which PHI can be obtained and/or played via the device 120. If the PHI requested to be played on the device 120 by the user is associated with a benefit claim that is one of the allowable types or categories of claims, then the device 102 and/or the device 120 can allow the requested PHI to be obtained and/or played. If the PHI requested to be played on the device 120 by the user is not associated with a claim that is an allowable type or category, then the device 102 and/or the device 120 can prevent the requested PHI to be obtained and/or played.

Conversely, the user may input an identification of one or more categories of benefit claims (via the device 102 and/or the device 120) that indicates which PHI is not allowed to be obtained and/or played via the device 120. If the PHI requested to be played on the device 120 by the user is associated with a benefit claim that is one of these disallowed types or categories of claims, then the device 102 and/or the device 120 prevents the requested PHI from being obtained and/or played. If the PHI requested to be played on the device 120 by the user is not associated with a claim that is a disallowed type or category, then the device 102 and/or the device 120 can allow the requested PHI to be obtained and/or played.

As another example, the user may restrict what PHI can be obtained and/or presented based on a patient identification. For example, the user may only want the PHI associated with one or more patients to be played, while PHI associated with other patients is not allowed to be obtained and/or played. This may occur when the user wants to hear the PHI associated with him or her, or with a relative (e.g., a parent or child) of the user. The user may input an identification of the patient (via the device 102 and/or the device 120), and the device 102 and/or the device 120 can allow only the PHI contained within medical records of the identified patient to be obtained and/or played. If the PHI requested to be played on the device 120 by the user is not contained within a record of the identified patient, then the device 102 and/or the device 120 can prevent the requested PHI to be obtained and/or played.

Optionally, the user may input an identification of the patient (via the device 102 and/or the device 120), and the device 102 and/or the device 120 can prevent the PHI contained within medical records of the identified patient from being obtained and/or played. If the PHI requested to be played on the device 120 by the user is not contained within a record of the identified patient, then the device 102 and/or the device 120 can allow the requested PHI to be obtained and/or played.

Figure 2:
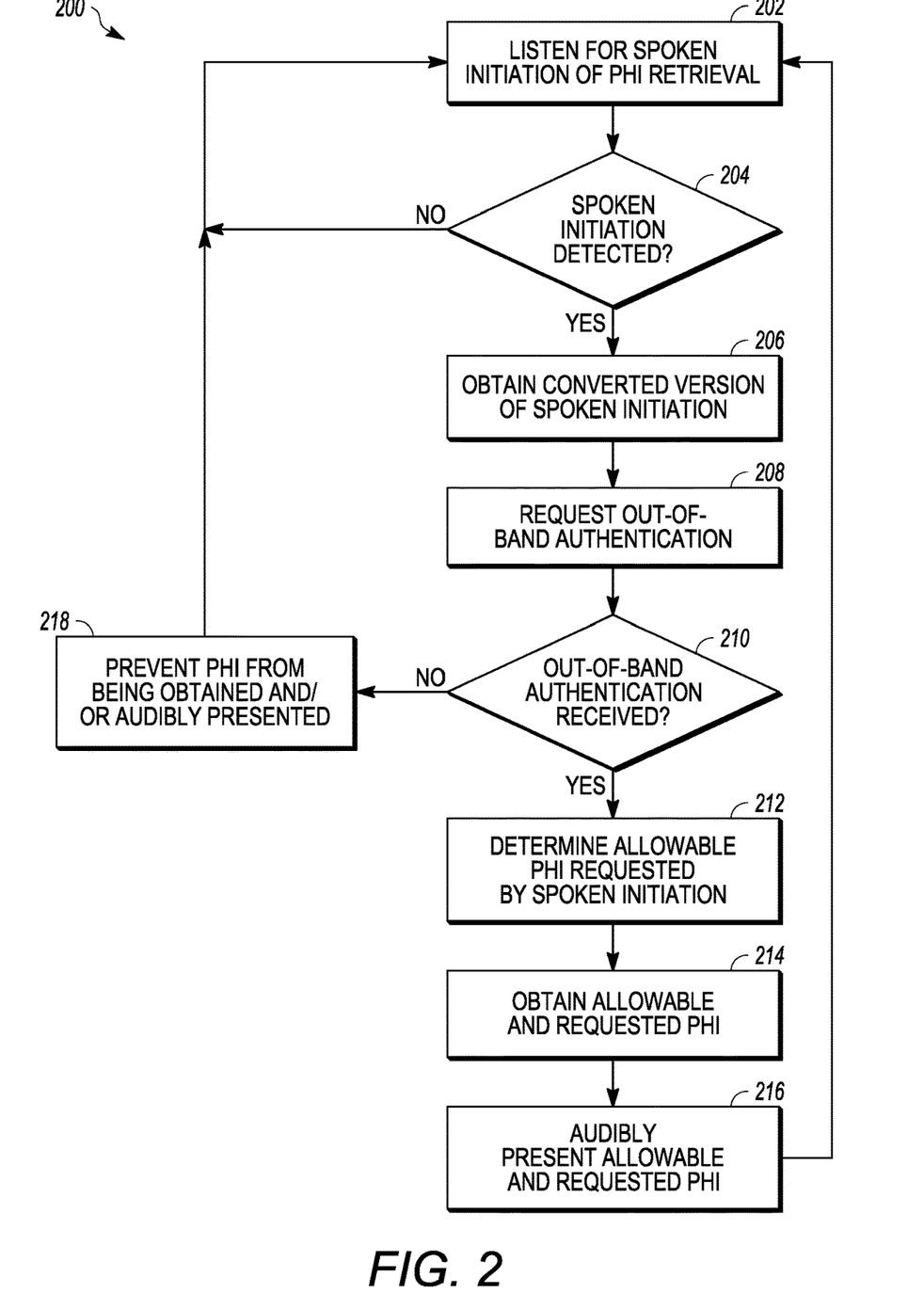
FIG. 2 illustrates a flowchart of one example of a method for authenticating access to PHI.

FIG. 2 illustrates a flowchart of one example of a method 200 for authenticating access to PHI. The method 200 can represent operations performed to determine whether a person using a voice-controlled electronic device can access PHI and have the voice-controlled electronic device audibly present the PHI via one or more speakers. The method 200 can represent operations performed by one or both of the voice-controlled device 102 and/or the user-controlled device 120.

At 202, an electronic device listens for spoken initiation of retrieval of PHI (or other confidential and/or private information). For example, the voice-controlled device 102 can have one or more microphones that detect spoken words that request PHI be played via one or more speakers of the voice-controlled device 102 (or of another device that is communicatively coupled with the voice-controlled device 102).

At 204, a determination is made as to whether the spoken initiation is detected. For example, the processors 106 of the voice-controlled device 102 can determine whether the input device 104 (e.g., a microphone) detected a voice requested PHI. The processors 106 may determine if a predetermined or designated phrase is spoken that triggers the retrieval of PHI.

If a spoken initiation is detected, then the processors 106 of the voice-controlled device 102 can implement one or more processes for determining what PHI is requested, whether the person requesting the PHI is authorized to access the PHI, to retrieve the requested PHI, and to present (e.g., play on a speaker) the requested PHI to the authorized user, dependent upon the outcome of the processes. As a result, flow of the method 200 can proceed toward 206. Otherwise, the processors 106 of the voice-controlled device 102 can continue listening for a spoken initiation or trigger, and flow of the method 200 can return to 202 (or may terminate).

At 206, a converted version of the spoken initiation or trigger is obtained. The converted version can be a text version of the spoken words. The converted version can be created by the processors 106 of the voice-controlled device 102, or the processors 106 can communicate an audio recording of the spoken initiation or trigger to another system or device (e.g., the conversion system 118) to generate the converted version of the spoken initiation or trigger. Optionally, different software applications 108 running on the voice-controlled device 102 can detect the spoken initiation (with one application 108) and create the converted version of the spoken initiation (with another application 108).

At 208, out-of-band authentication information is requested. In one example, one or more of the applications 126A-C can direct the processors 124 of the user-controlled device 120 to examine the text and request out-of-band authentication information from a user. Alternatively, an application 108 of the voice-controlled device 102 can request this information from the user, with this application 108 being a separate or different application 108 from the application 108 that detected and/or converted the spoken initiation. The authentication information can include a unique code, demographic information, a previously answered preference, biometric data, or the like, as described above.

At 210, a determination is made as to whether the correct authentication information is received. The processors 124 of the user-controlled device 120 can determine whether the information provided in response to the request in 208 matches or satisfies one or more criteria. For example, a determination can be made as to whether the unique code, demographic information, previously answered preference, and/or biometric data matches previously identified or authenticated codes, demographic information, preferences and/or biometric data. If the provided information matches or satisfies the criteria, then the user is authenticated to receive at least some PHI. As a result, flow of the method 200 proceeds toward 212. But, if the provided information does not match or satisfy the criteria, then the user is not authenticated to receive the PHI. As a result, flow of the method 200 can return toward 202 or can terminate.

At 212, a determination of what PHI can be played is determined. The processors 124 of the user-controlled device 120 can determine what PHI was requested (from the spoken initiation or trigger) and what preferences or limits have been previously established to dictate which portions of the PHI can be shared. For example, the applications 126 may have default or user-defined restrictions on which categories of PHI can be played, which date ranges of PHI can be played, which healthcare provider-generated PHI can be played, which categories of PHI related to healthcare benefit claims can be played, which patients can have PHI associated with those patients played, etc.

At 214, the PHI that is both requested and that falls within the portions of PHI that can be shared is obtained. The PHI can be obtained by the processors 106 of the voice-controlled device 102 (e.g., from the data stores 134) via the one or more networks 116. Optionally, the PHI can be obtained by the processors 124 of the user-controlled device 120 (e.g., from the data stores 134) via the one or more networks 116, and then communicated to the voice-controlled device 102.

At 216, the PHI that is requested, authenticated to be played, and obtained is then audibly presented. For example, one or more speakers of the voice-controlled device 102 can play an audio file that contains or represents the PHI that was obtained. The voice-controlled device 102 can continue to obtain and present additional PHI to the user so long as the authentication of the user is maintained or does not expire. Flow of the method 200 can then return to 202 or terminate.

Figure 3:
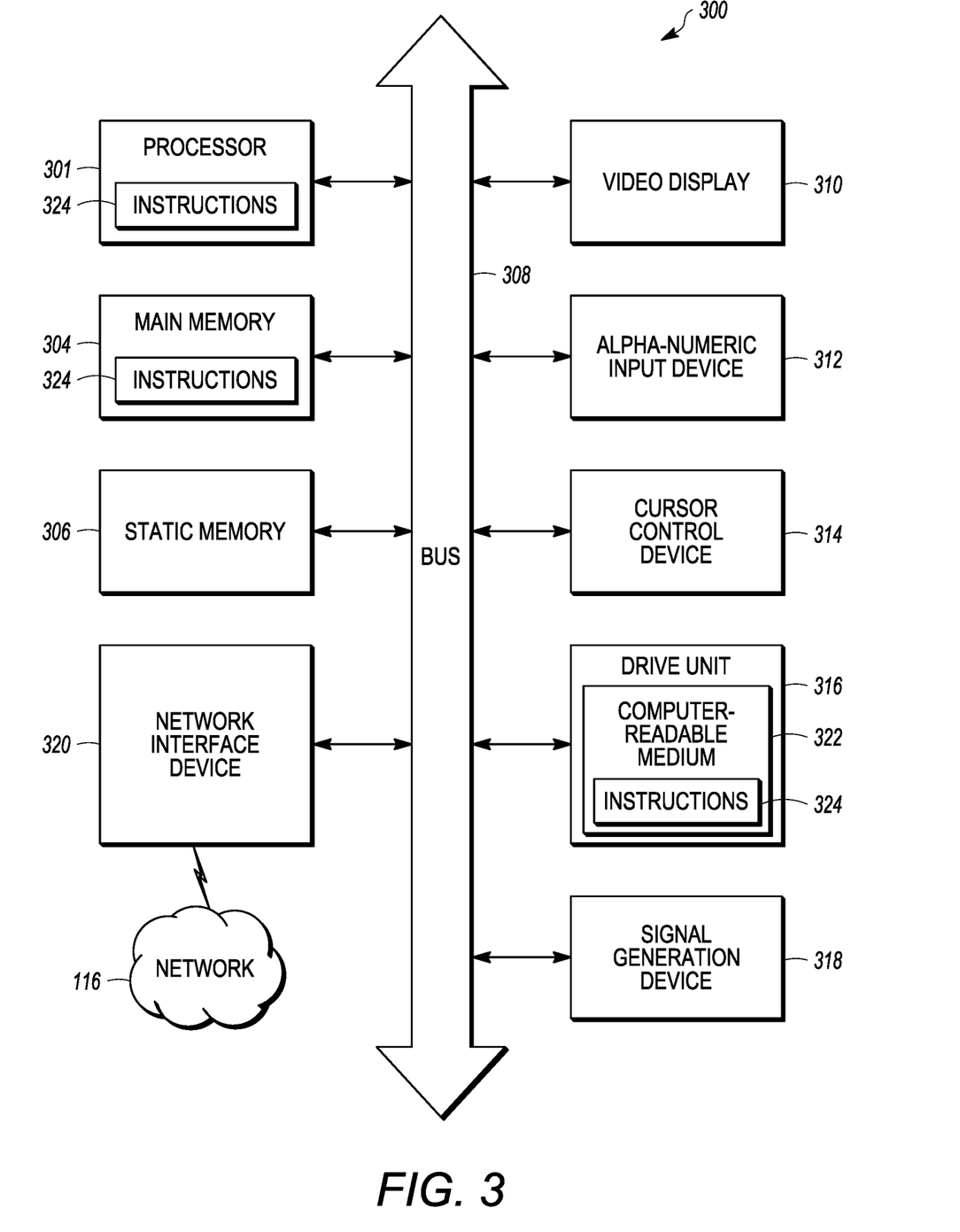
FIG. 3 shows a block diagram of an electronic device, which can represent a voice-controlled device and/or a user-controlled device shown in FIG. 1.

FIG. 3 shows a block diagram of an electronic device 300, which can represent the voice-controlled device 102 and/or the user-controlled device 120. The device 300 is shown as a computer system within which a set of instructions may be executed causing the machine to perform any one or more than one methods, processes, operations, or methodologies discussed herein. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 300 includes one or more processors 301 (e.g., a central processing unit (CPU), a graphics processing unit (GPU) or both, etc.), a main memory 302 and a static memory 304, which communicate with each other via a bus 306. The computer system 300 further includes a video display unit 308 (e.g., a liquid crystal display (LCD) or a cathode ray tube (CRT), etc.). The computer system 300 also includes an alphanumeric input device 310 (e.g., a physical or displayed keyboard, etc.), a cursor control device 322 (e.g., a mouse, etc.), a drive unit 312, a signal generation device 314 (e.g., a speaker, etc.) and a network interface device 316.

The drive unit 312 includes a computer readable medium 318 (CPU Readable Medium in FIG. 3) on which is stored one or more than one sets of instructions 320 (e.g., software, etc.) embodying any one or more than one methodologies or functions described herein. The instructions 320 may also reside, completely or at least partially, within the main memory 302 and/or within the processor 410 during execution thereof by the computer system 300, the main memory 302 and the processor 410 also constituting non-transitory computer readable media. When loaded with the instructions 320, the processor 410 is a machine dedicated to only the present processes and methodologies.

The instructions 320 may further be transmitted or received over the network 110 via the network interface device 316.

While the computer-readable medium 318 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that can store or encoding a set of instructions for execution by the machine and that cause the machine to perform any one or more than one methodologies of the present invention. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The term "based on" or using, as used herein, reflects an open-ended term that can reflect others elements beyond those explicitly recited.

Certain systems, apparatus, applications or processes are described herein as including several modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

The inventive subject matter may be represented in a variety of different embodiments of which there are many possible permutations.

In one embodiment, a method for authenticating access to PHI includes receiving a converted version of a spoken initiation at one or more of a second device or a second application operating on a first device responsive to a first application operating on the first device receiving the spoken initiation of a retrieval of PHI. The method also includes requesting out-of-band authentication information from a user via the one or more of the second device or the second application responsive to receiving the converted version of the spoken initiation. The out-of-band authentication information that is requested contains different information than the spoken initiation of the retrieval of the PHI. The method also includes determining whether the out-of-band authentication information received from the user at the one or more of the second device or the second application satisfies an authentication criterium associated with the user, obtaining the PHI requested by the user via the spoken initiation provided to the first device responsive to the out-of-band authentication information, and presenting the PHI requested by the user via the first device.

Optionally, the PHI requested by the user is audibly presented via one or more speakers of the first device.

Optionally, the converted version of the spoken initiation that is received at the one or more of the second device or the second application is a text-based conversion of the spoken initiation.

Optionally, the method also includes identifying a patient represented by the PHI based on information contained within the converted version of the spoken initiation at the one or more of the second device or the second application, and determining the authentication criterium based on the patient represented by the PHI.

Optionally, the out-of-band authentication information that is requested via the one or more of the second device or the second application includes one or more of a fingerprint scan of the user, a retinal scan of the user, or a vocal sample from the user that is received by the second device.

Optionally, the out-of-band authentication information that is requested via the one or more of the second device or the second application includes one or more of a personal identification number, a numerical string, a text string, or an alpha-numeric string that is received by the second device.

Optionally, the personal identification number, the numerical string, the text string, or the alpha-numeric string that is received by the one or more of the second device or the second application is provided on a pharmaceutical container.

Optionally, the PHI is presented via the first device for no longer than a predetermined designated time period.

Optionally, the method also includes modifying the predetermined designated time period based on input received from the user at the one or more of the second device or the second application.

Optionally, the method also includes receiving, at the one or more of the second device or the second application, a user-defined restriction on which portions of the PHI are presented via the first device. One or more of obtaining the PHI or presenting the PHI can be limited to the portions of the PHI that are permitted to be presented based on the user-defined restriction received at the one or more of the second device or the second application.

Optionally, the user-defined restriction limits the portions of the PHI that are obtained, presented, or both obtained and presented based on one or more of a date range provided by the user, a healthcare provider identified by the user, a healthcare benefit claim type identified by the user, or an identification of a patient associated with the PHI and that was provided by the user.

In another example, a method for authenticating access to PHI includes receiving a spoken initiation of a retrieval of PHI at a first application operating on a first device from a user, determining whether the spoken initiation is spoken by an approved person using vocal recognition, requesting an out-of-band authentication information from the user at one or more of a second device associated with the user or a second application operating on the first device, obtaining the PHI identified by the user in the spoken initiation (from a third device) responsive to determining that the spoken initiation is spoken by the approved person and the out-of-band authentication information, and presenting the PHI requested by the user via the first device.

Optionally, the PHI requested by the user is audibly presented via one or more speakers of the first device.

Optionally, the method also includes identifying a patient represented by the PHI based on information contained within the spoken initiation provided by the user, and determining whether the spoken initiation is spoken by the approved person based on the patient represented by the PHI.

Optionally, the out-of-band authentication information that is requested includes one or more of a fingerprint scan of the user, a retinal scan of the user, a personal identification number, a numerical string, a text string, or an alpha-numeric string.

Optionally, the personal identification number, the numerical string, the text string, or the alpha-numeric string is provided on a pharmaceutical container.

Optionally, the PHI is presented via the first device for no longer than a predetermined designated time period.

Optionally, the method also includes modifying the predetermined designated time period based on input received from the user at the first device.

Optionally, the method also includes modifying the predetermined designated time period based on input received from the second device, the third device, or a shortest time period at the second device or the third device.

Optionally, the method also includes receiving a user-defined restriction on which portions of the PHI are presented via the first device, where one or more of obtaining the PHI or presenting the PHI is limited to the portions of the PHI that are permitted to be presented based on the user-defined restriction that is received.

Optionally, the user-defined restriction limits the portions of the PHI that are obtained, presented, or both obtained and presented based on one or more of a date range provided by the user, a healthcare provider identified by the user, a healthcare benefit claim type identified by the user, or an identification of a patient associated with the PHI and that was provided by the user.

In another example, a method for authenticating access to PHI includes, responsive to a first application operating on a first device receiving a spoken initiation of a retrieval of PHI, receiving a text version of the spoken initiation at one or more of a second device or a second application operating on the first device, requesting out-of-band authentication information from a user via the one or more of the second device or the second application responsive to receiving the text version of the spoken initiation, the out-of-band authentication information that is requested containing different information than the spoken initiation of the retrieval of the PHI, identifying a patient represented by the PHI based on information contained within the text version of the spoken initiation at the one or more of the second device or the second application, determining an authentication criterium based on the patient represented by the PHI, determining whether the out-of-band authentication information received from the user at the one or more of the second device or the second application satisfies the authentication criterium associated with the user, obtaining the PHI requested by the user via the spoken initiation provided to the first device responsive to the out-of-band authentication information, and audibly presenting the PHI requested by the user via one or more speakers of the first device.

Optionally, the out-of-band authentication information that is requested via the one or more of the second device or the second application includes one or more of a fingerprint scan of the user, a retinal scan of the user, a vocal sample from the user, a personal identification number, a numerical string, a text string, or an alpha-numeric string that is received by the one or more of the second device or the second application.

Optionally, the method also includes receiving, at the second device, a user-defined restriction on which portions of the PHI are presented via the first device, where one or more of obtaining the PHI or presenting the PHI is limited to the portions of the PHI that are permitted to be presented based on the user-defined restriction received at the one or more of the second device or the second application.

Although embodiments of the inventive subject matter have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The present description uses various example embodiments related to pharmacy data and PHI to illustrate specific examples of using various processes to protect regulated, secret, or restricted information from improper dissemination on voice activated devices. Methods on and systems using voice activated devices can be in portable electronic devices and the present disclosure provides user validation to disclose personal or protected information. The portable electronic device can be a multi-function electronic device. The portable electronic device can also interact with a media system, which may also have access to the protected information, e.g., broadcast the information.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C." For example, each of the phrases "at least one of A, B, or C," "one or more of A, B, or C." "at least one of A, B, and C," and "one or more of A, B, and C" includes (1) only A, (2) only B, (3) only C, (4) A and B, (5) A and C, (6) B and C, or (7) A, B, and C.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. A memory circuit can be used to execute tasks as described herein. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc). The computer-readable medium can be used to store the tasks for execution on a device as described herein.

The apparatuses and methods described in this application may be partially or fully implemented by a special purpose computer created by configuring a general purpose computer to execute one or more than one particular functions embodied in computer programs. The functional blocks and flow-chart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A method comprising:
responsive to a first device receiving a spoken initiation of a retrieval of private health information (PHI), receiving a converted version of the spoken initiation at a second device that is different and separate from the first device;
requesting out-of-band authentication information from a user via the second device responsive to receiving the converted version of the spoken initiation, the out-of-band authentication information that is requested containing different information than the spoken initiation of the retrieval of the PHI;
determining whether the out-of-band authentication information received from the user at the second device satisfies an authentication criterium associated with the user;
obtaining the PHI requested by the user via the spoken initiation provided to the first device responsive to the out-of-band authentication information satisfying the authentication criterium;
presenting the PHI requested by the user via the first device; and
further comprising:
receiving user limitations that restrict the PHI that is presented via the first device, the user limitations including one more of a user-configurable time period over which the PHI is permitted to be presented via the first device, a user-defined category of the PHI that is permitted to be presented via the first device, a user-defined date range that restricts the PHI that is presented via the first device to the PHI that was obtained over the user-defined date range, a user-identified provider identification that restricts the PHI that is presented via the first device to the PHI provided by a provider associated with the user-identified provider identification, or a user-identified type of benefit claim that restricts the PHI that is permitted to be presented via the first device to the user-identified type of benefit claim.

2. The method of claim 1, wherein the PHI requested by the user is audibly presented via one or more speakers of the first device.

3. The method of claim 1, wherein the converted version of the spoken initiation that is received at the second device is a text-based conversion of the spoken initiation.

4. The method of claim 1, further comprising:
identifying a patient represented by the PHI based on information contained within the converted version of the spoken initiation at the second device; and
determining the authentication criterium based on the patient represented by the PHI.

5. The method of claim 1, wherein the out-of-band authentication information that is requested via the second device includes one or more of a fingerprint scan of the user, a retinal scan of the user, or a vocal sample from the user that is received by the second device.

6. The method of claim 1, wherein the out-of-band authentication information that is requested via the second device includes one or more of a personal identification number, a numerical string, a text string, or an alpha-numeric string that is received by the second device.

7. The method of claim 6, wherein the personal identification number, the numerical string, the text string, or the alpha-numeric string that is received by the second device is provided on a pharmaceutical container.

8. The method of claim 1, further comprising:
receiving, at the second device, one or more user-defined restrictions on which portions of the PHI are presented via the first device,
wherein one or more of obtaining the PHI or presenting the PHI is limited to the portions of the PHI that are permitted to be presented based on the one or more user-defined restrictions received at the second device.

9. The method of claim 8, wherein the one or more user-defined restrictions limit the portions of the PHI that are obtained, presented, or both obtained and presented based on one or more of a date range provided by the user, a healthcare provider identified by the user, a healthcare benefit claim type identified by the user, or an identification of a patient associated with the PHI and that was provided by the user.

10. A method comprising:
receiving a spoken initiation of a retrieval of private health information (PHI) at a first device from a user;
determining whether the spoken initiation is spoken by an approved person using vocal recognition;
requesting an out-of-band authentication information from the user at a second device that is different and separate from the first device;
obtaining the PHI identified by the user in the spoken initiation, from a third device, responsive to determining that the spoken initiation is spoken by the approved person and the out-of-band authentication information satisfies an authentication criterium;
presenting the PHI requested by the user via the first device; and
further comprising receiving one or more user-defined restrictions that restrict the PHI that is presented via the first device, the one or more user-defined restrictions including a user-configurable time period over which the PHI is permitted to be presented via the first device, a user-defined category of the PHI that is permitted to be presented via the first device, a user-defined date range that restricts the PHI that is presented via the first device to the PHI that was obtained over the user-defined date range, a user-identified provider identification that restricts the PHI that is presented via the first device to the PHI provided by a provider associated with the user-identified provider identification, and a user-identified type of benefit claim that restricts the PHI that is permitted to be presented via the first device to the user-identified type of benefit claim.

11. The method of claim 10, wherein the PHI requested by the user is audibly presented via one or more speakers of the first device.

12. The method of claim 10, further comprising:
identifying a patient represented by the PHI based on information contained within the spoken initiation provided by the user; and
determining whether the spoken initiation is spoken by the approved person based on the patient represented by the PHI.

13. The method of claim 10, wherein the out-of-band authentication information that is requested includes one or more of a fingerprint scan of the user, a retinal scan of the user, a personal identification number, a numerical string, a text string, or an alpha-numeric string.

14. The method of claim 13, wherein the personal identification number, the numerical string, the text string, or the alpha-numeric string is provided on a pharmaceutical container.

15. The method of claim 10, wherein the PHI is presented via the first device for no longer than a predetermined designated time period.

16. The method of claim 15, further comprising:
modifying the predetermined designated time period based on input received from the user at the first device.

17. The method of claim 15, further comprising:
modifying the predetermined designated time period based on input received from the second device, the third device, or a shortest time period at the second device or the third device.

18. The method of claim 10, further comprising:
receiving a user-defined restriction on which portions of the PHI are presented via the first device,
wherein one or more of obtaining the PHI or presenting the PHI is limited to the portions of the PHI that are permitted to be presented based on the user-defined restriction that is received.

19. The method of claim 18, wherein the user-defined restriction limits the portions of the PHI that are obtained, presented, or both obtained and presented based on one or more of a date range provided by the user, a healthcare provider identified by the user, a healthcare benefit claim type identified by the user, or an identification of a patient associated with the PHI and that was provided by the user.

20. A method comprising: responsive to a first device receiving a spoken initiation of a retrieval of private health information (PHI), receiving a text version of the spoken initiation at a second device that is different and separate from the first device;
requesting out-of-band authentication information from a user via the second device responsive to receiving the text version of the spoken initiation, the out-of-band authentication information that is requested containing different information than the spoken initiation of the retrieval of the PHI;
identifying a patient represented by the PHI based on information contained within the text version of the spoken initiation at the second device;
determining an authentication criterium based on the patient represented by the PHI; determining whether the out-of-band authentication information received from the user at the second device satisfies the authentication criterium associated with the user;
obtaining the PHI requested by the user via the spoken initiation provided to the first device responsive to the out-of-band authentication information satisfying the authentication criterium;
audibly presenting the PHI requested by the user via one or more speakers of the first device; and
further comprising receiving one or more user-defined restrictions that restrict the PHI that is presented via the first device, the one or more user-defined restrictions including a user-configurable time period over which the PHI is permitted to be presented via the first device, a user-defined category of the PHI that is permitted to be presented via the first device, a user-defined date range that restricts the PHI that is presented via the first device to the PHI that was obtained over the user-defined date range, a user-identified provider identification that restricts the PHI that is presented via the first device to the PHI provided by a provider associated with the user-identified provider identification, and a user-identified type of benefit claim that restricts the PHI that is permitted to be presented via the first device to the user-identified type of benefit claim.

21. The method of claim 20, wherein the out-of-band authentication information that is requested via the second device includes one or more of a fingerprint scan of the user, a retinal scan of the user, a vocal sample from the user, a personal identification number, a numerical string, a text string, or an alpha-numeric string that is received by the second device.

22. The method of claim 20, further comprising:
receiving, at the second device, a user-defined restriction on which portions of the PHI are presented via the first device,
wherein one or more of obtaining the PHI or presenting the PHI is limited to the portions of the PHI that are permitted to be presented based on the user-defined restriction received at the second device.

* * * * *